United States Patent [19]
Camp et al.

[11] Patent Number: 5,964,905
[45] Date of Patent: Oct. 12, 1999

[54] SCENTED CANDLE GEL

[75] Inventors: William R. Camp, Reading; Jeffrey L. Vollenweider, Shillington; Wendy J. Schutz, Pottstown, all of Pa.

[73] Assignee: Sara Lee Corporation, Douglassville, Pa.

[21] Appl. No.: 09/082,760

[22] Filed: May 21, 1998

[51] Int. Cl.⁶ .................................................. C11C 5/00
[52] U.S. Cl. ........................................... 44/275; 431/288
[58] Field of Search ................................ 44/275; 431/288

[56] References Cited

U.S. PATENT DOCUMENTS

| | | | |
|---|---|---|---|
| 3,771,445 | 11/1973 | Campbell et al. | 44/275 |
| 3,940,233 | 2/1976 | Fox et al. | 44/275 |
| 4,110,261 | 8/1978 | Newsland | 44/275 |
| 5,578,089 | 11/1996 | Elsamaloty | 44/275 |

FOREIGN PATENT DOCUMENTS

WO97/08282  3/1997  WIPO .

*Primary Examiner*—Cephia D. Toomer
*Attorney, Agent, or Firm*—John Lezdey & Assoc.

[57] ABSTRACT

The invention provides a scented gel candle which is flash proof and provides a greater scent. The candle consists of a container having a candle body of a triblock copolymer and hydrocarbon oil having a high flash point. A wick is located in the candle body and is preferably of an unwaxed diameter of about 3/64 to 5/64 inch. The use of the combination of an appropriately sized wick and the high flash hydrocarbon oil provides a safe candle with a satisfactory release of a scent.

16 Claims, No Drawings

SCENTED CANDLE GEL

FIELD OF THE INVENTION

The present invention relates to a flash-proof candle comprising a high flash hydrocarbon oil gel in combination with a scent and a wick with a safety clip. More particularly, there is provided within a container, a gel candle comprising a wick and a body of a triblock copolymer, a hydrocarbon oil having a high flash point and a source for a scent.

BACKGROUND OF THE INVENTION

Gel candles have been used for dispensing a controlled release of different scents, phenomones, insect repellents, and the like.

U.S. Pat. No. 5,705,175 to Johnson, which is incorporated herein by reference, discloses a hydrocarbon gel in which one or more block copolymers are derived from styrene-rubber block units, a hydrocarbon oil and an insecticide or insect repellant. The composition is for emitting the scents at low temperatures and for use in skin applications. A candle is not disclosed.

U.S. Pat. No. 5,578,089 to Elsamalotz discloses a clear candle made from a gel comprising mineral oil containing at least one diblock copolymer and at least one triblock copolymer. The combination disclosed forms a candle which can overheat and is subject to flashing when in a confined container and burned for a long period of time.

In aromatherapy, the different scents from essential oils trigger a mind-body reaction, which have been indicated as alleviating physical and emotional symptoms such as muscle pain, nervousness, irritability, headaches and lethargy.

In aromatherapy, oils, herbs such as bergamot, geranium, lavender, tea tree, lemon, peppermint and sage have been used to treat acne and oily skin.

The essential oils of rose, aloe, jasmine, and orange have been used to treat dry skin.

For stress and anxiety, the essential oils for aromatherapy are allspice, cedarwood, melissa, orange and sandalwood.

Essential oils derived from impatiens, rose, iris, holly snapdragons and other plants have been found to be useful for aromatherapy alone or in a combination.

The diffusion of the essential oils by means of the present invention provides the same reaction as spraying the essential oils in a room.

Many of the terpenes, for example, menthol, thymol, eucalyptus, and the like have been found to be useful in room vaporizers and sprays to disinfect or to provide a decongestant effect. It would be advantageous to use the terpenes in combination with the candles of the present invention. The use of the specific hydrocarbon oils of the invention together with a larger wick causes a greater pooling of the candle body and thereby a greater release of scent.

It is understood that the term "burn point" with regard to hydrocarbon oil gel candle relates to the temperature at which a fire will be sustained.

"Flash point" relates to the temperature at which the hydrocarbon oil gives off a vapor sufficient to form an ignitable mixture with air. This temperature is generally lower than the burn point and relates to the type of volatiles in the oil.

It is common in the industry to provide a metal clip at the base of a wick. Generally, the base of the metal clip has a base diameter of 15–20 mm and a neck or stem height of about 2 mm.

The wicks of candles are usually waxed and formed by strands of cotton or other threads. The nomenclature varies within the industry. For example, wicking material prepared by Atkins & Pierce having a designation of 44-28-18z refers to a wick wound with a 44 gear (provides relative tightness) size of wick having 28 strands of a type 18 cotton and a zinc core.

Flat braided wicks can be used, however such wicks are more common in large pillar type candles. The dimensions for a flat braided wick are generally by the total number of threads used to prepare the wick, for example, a 15 ply flat braid wick would contain 15 threads, perhaps 5 threads in each of 3 strands which are braided.

SUMMARY OF THE INVENTION

According to the present invention, there is provided a flash proof and explosion proof gel candle comprising:

a container;

a gel body within said container; and a wick located in said body, wherein said body comprises about 1 to 20 weight percent of a triblock copolymer comprising segments of polystyrene and rubber, about 80 to 98 weight percent of a hydrocarbon oil having a high flash point, and about 0.5 to 10 weight percent of a scent.

Advantageously, the scent is derived from an essential oil so as to provide aromatherapy.

The candle further contains an appropriately sized wick with a taller wick clip stem.

It is a general object of the invention to provide a safe gel candle which also contains a scent of sufficient intensity to fragrance a living area such as a kitchen, dining room, bath or den.

It is another object of the invention to provide a gel candle which can be used in connection with aromatherapy.

It is a further object of the invention to provide a gel candle having a high intensity.

It is a still further object of the invention to provide a gel candle that is colored with dye and sufficiently stable to avoid dye degradation/discoloration when exposed to extended periods of ultraviolet or visible light.

It is yet another object of the invention to provide a gel candle having an aesthetic appearance.

DESCRIPTION OF THE PREFERRED EMBODIMENTS

In accordance with one embodiment of the invention, there is provided a safe gel candle which does not flash when burned. The gel candle comprises:

a container;

a gel body within said container; and a wick located within said gel body, said gel body comprising about 1 to 20 weight percent of a triblock copolymer comprising segments of polystyrene and rubber, about 80 to 98 weight percent of a hydrocarbon oil having a flash point greater than 440° F. and at least about 0.5 weight percent, preferably about 0.5 to 10 weight percent, of a scent. Preferably, the resultant candle provides a burn or fragrance sensory score of at least 3.

Commercially available triblock copolymers, which are useful in the present invention, are sold under the trademark KPATON® by Shell Chemical Company. The KRATON® polymers are described as thermoplastic elastomers having block segments of polystyrene and rubber and/or comonomer units. The KRATON® G series polymers comprise styrene-ethylenebutylene-styrene type structures. Other triblock copolymers include styrene-butadiene-styrene and styrene-isoprene-styrene. The preferred rubbers of the triblock copolymers are thermoplastic.

The non-flashing and other advantages achieved by the present invention result from the use of hydrocarbon oils having a flash point at least about 440° F. or greater, generally between 490 and 500° F., which may be used alone or admixture.

The hydrocarbon oils which can be used in the present invention include the natural or synthetic grade cosmetic oils, for example, mineral oils, paraffinic oils, isoparaffinic oils, napthenic oils, and the like which have a flash point at greater then about 440° F. Such oils are sold by Petro Canada under the trademarks PURITY 50 and LUMINOL T 500 and by Witco under the trademark SEMTOL 500. In general, the hydrocarbon oils contain about 13 to 50 carbon atoms.

The gel consistency under the invention is controlled by varying the amount ratio and types of triblock copolymer. The higher the amount of copolymer, the stiffer the gel.

A wide variety of scents may be incorporated into the gel body including not only the conventional scents such as vanilla, citronella, burberry, floral, pine and the like, but also terpenes and essential oils. The combined or compounded fragrance should have a flash point of greater than 180° F., preferably at or above 200° F.

The essential oils used in the candle body of the invention are preferably those which are used for aromatherapy which were hereinbefore mentioned.

The preferred terpenes include menthol, thymol, eucalyptus, pinene, and the like.

Other additives which are common in the candle art may be used, for example, a colorant or dye. Other useful additives are at least one light absorber to improve shelf stability of the candle color when exposed to visible or ultraviolet light. Two preferred absorbers are ethylhexyl p-methoxycinnamate, sold under the name PARSOL® MCX by Roche and 2-(2-hydroxy-5-tert-octylphenyl) benzotriazole, sold under the name Cyasorb UV-5411 Light Absorber by Cytec. About 0.05 to 1% by weight of light absorber can be used.

Preferred gel candles of the invention can be prepared using the following ingredients:

| Ingredient | % w/w |
|---|---|
| Mineral oil | 85–90 |
| Triblock polymer | 5–10 |
| Scent | 2–10 |

Preferably, the gel is used with a wick having an unwaxed diameter of about 3/64 in. to about 5/64 in. which has a wick clip having a height of about 4–10 mm.

The following examples are presented to illustrate the invention and should not be considered as a limitation thereof. In these examples, parts are by weight per 100 weight parts of the composition (i.e. weight percent) unless otherwise indicated.

EXAMPLE 1

Preparation of candles:

Into a container is placed the hydrocarbon oil and the oil is heated to a temperature of about 250° F. The oil is stirred and about 1 to 20 weight percent of a triblock copolymer is added. The temperature is increased to about 350° F. and the mixture stirred until the copolymer is completely dissolved. The mixture is then cooled to about 250° F. and about 0.5 to 5 weight percent of a scent is added together with any colorant if a color is desired. The composition is mixed and then poured into pre-wicked containers at a temperature of about 240–250° F. The composition is then cooled and packaged.

EXAMPLE 2

Following the procedure of Example 1, the following gel candle was prepared:

| Ingredient | % w/w |
|---|---|
| Mineral oil (PURITY 50) | 87.9999 |
| Triblock polymer (KRATON G 1650) | 7.5000 |
| Scent (Vanilla) | 4.5000 |
| Dye (SOLVISOL yellow R) | 0.0001 |
| | 100.0000 |

In lieu of vanilla, there may be used other scents, such as, essential oils and terpenes.

Advantageously, the gel candle is used with a wick which is about 1/16 in. diameter and contains a safety clip of about 6 mm in height.

EXAMPLE 3

A comparative test was run between the gel candle of Example 2 and a single KRATON® and a low flash oil.

| Description | Candle of Example 2 | Candle of a Single KRATON with a low flash point oil |
|---|---|---|
| Burn Sensory (1) | 3.6 | 3.5 |
| Burn point (2) | 490° F.–510° F. | 310° F.–324° F. 402° F.–448° F. |
| Temperature profile (max. temp. of pool) | 307° F. | 1221° F. |
| Self ignition | 0 out of 6,381 | 2 out of 100 4 out of 96 |
| Wick clip neck size | 6 mm | 2 mm |
| Wick size | 44-28-18z | 44-32-18z |

(1) Score of 3 is acceptable, 4 is strong and <3 is unacceptable. The procedure to determine the sensory score of a gel candle is as follows:

Burn or Fragrance Sensory Test Procedure:

1. Candles, to be tested, are burned in an area outside[1] the test booths for one hour.

[1]Burn area should not be near the booths or in an area where participants will walk or be near before the test.

2. After one hour, candles are placed in the test booths[2] and allowed to burn for five minutes before testing.

[2]Test booths were 12' by 10' offices with the air out-take vent covered.

3. Participants enter the booths together, smell the air, then leave the booth together.

4. Participants rate each booth for intensity, quality and overall scent. The scale for each parameter is 1–5, with 3 being acceptable or just right, 1 is unacceptable or very weak, and 5 is excellent or very strong.

5. The results are calculated and statistical differences are determined.

(2) Temperature at which the molten candle gel will support a flame on entire surface.

The gel candle of the invention had better safety. The use of high flash point oil allows for a wick of sufficient size to be used that generates sufficient heat to cause the release from the candle of an acceptable level of scent, without causing a safety problem.

EXAMPLE 4

A test was conducted on gel candles of the invention wherein the hydrocarbon oil (mineral oil was varied together with the scent and wick size to determine the sensory score of the candle). A sensory score of at least 3.0 is acceptable. The results were as follows:

| Fragrance | Oil | Wick | Sensory Score |
| --- | --- | --- | --- |
| Vanilla | High Flash Oil | 44-28-18z | 3.06 |
|  | High Flash Oil | 36-24-24z | 2.69 |
| Fresh | High Flash Oil | 44-28-18z | 3.87 |
|  | High Flash Oil | 36-24-24z | 2.69 |
| Fresh | Low Flash Oil | 36-24-24z | 1.93 |
| Blossom | High Flash Oil | 44-28-18z | 4.02 |
|  | High Flash Oil | 36-24-24z | 3.00 |
| Blossom | Low Flash Oil | 36-24-24z | 3.31 |
| Berry | High Flash Oil | 44-28-18z | 3.13 |
|  | High Flash Oil | 36-24-24z | 2.50 |
| Berry | Low Flash Oil | 36-24-24z | 2.64 |

The use of a smaller wick (36-24-24z), generally does not achieve acceptable product performance as measured by the sensory score. In one experiment, i.e. Blossom, an acceptable sensory score is obtained, however, the candle is not considered safe due to the use of low flash oil. This further underscores the need for high flash oil in conjunction with a larger wick to achieve acceptable release of scent.

EXAMPLE 5

Following the procedure of Example 1, a gel candle is prepared having the following ingredients:

| Ingredient | % w/w |
| --- | --- |
| Poly(styrene-ethylenebutylene-styrene) triblock copolymer | 5.0 |
| SEMTOL 500 | 90.0 |
| Limonene | 5.0 |
|  | 100 |

In lieu, of Limonene, there may be used other essential oils such as rose oil, orange oil, sage oil, and the like.

About 0.5% by weight of a light absorber could be added.

What is claimed is:

1. A gel candle comprising:
   a container;
   a gel body within said container; and
   a wick located within said gel body, said gel body consisting essentially of about 1 to 20 weight percent of a triblock copolymer wherein said triblock copolymer is selected from the group consisting of poly(styrene-ethylene-butylene-styrene), poly(styrene-butadiene-styrene), and poly(styrene-isoprene-styrene), and about 80 to 98 weight percent of a hydrocarbon oil having a flash point greater than 440° F.

2. The gel candle of claim 1 wherein said hydrocarbon oil is a mineral oil.

3. The gel candle of claim 1 including a scent.

4. The gel candle of claim 3 wherein the scent has a flash point greater than 180° F.

5. The gel candle of claim 3 wherein said scent comprises about 0.5 to 10 weight percent.

6. The gel candle of claim 3 wherein said scent comprises a terpene.

7. The gel candle of claim 6 wherein said terpene is selected from the group consisting of menthol, thymol and a terpene derived from eucalyptus.

8. The gel candle of claim 3 wherein said scent comprises an essential oil.

9. The gel candle of claim 8 wherein said essential oil is selected from the group consisting of lavender, lemon, peppermint, rose and sage.

10. The gel candle of claim 1 wherein said wick has an unwaxed diameter of about 3/64 inch to about 5/64 inch.

11. The gel candle of claim 1 including a wick clip, said clip having a height of about 4 to 10 mm.

12. The gel candle of claim 1 wherein said candle has a fragrance sensory score of at least 3.0.

13. The gel candle of claim 1 including at least one light absorber.

14. A gel candle comprising:
    a container;
    a gel body within said container; and
    a wick having an unwaxed diameter of about 3/64 to 5/64 inch and a wick clip having a height of about 4 to 10 mm, said gel body consisting essentially of about 80 to 98 weight percent of a mineral oil having a flash point greater than about 440° F., about 5 to 10 weight percent of a triblock copolymer, wherein said triblock copolymer is selected from the group consisting of poly (styrene-ethylene-butylene-styrene), poly(styrene-butadiene-styrene), and poly(styrene-isoprene-styrene), and and about 2 to 10 weight percent of a scent having a flash point greater than 180° F.

15. The gel candle of claim 11 wherein said gel body contains a dye.

16. The gel candle of claim 14 wherein said gel body contains at least one light absorber.

* * * * *